(12) United States Patent
Umehara

(10) Patent No.: US 10,012,596 B2
(45) Date of Patent: Jul. 3, 2018

(54) APPEARANCE INSPECTION APPARATUS AND APPEARANCE INSPECTION METHOD

(71) Applicant: JTEKT CORPORATION, Osaka-shi, Osaka (JP)

(72) Inventor: Jiro Umehara, Toyonaka (JP)

(73) Assignee: JTEKT CORPORATION, Osaka (JP)

( * ) Notice: Subject to any disclaimer, the term of this patent is extended or adjusted under 35 U.S.C. 154(b) by 0 days.

(21) Appl. No.: 15/669,527

(22) Filed: Aug. 4, 2017

(65) Prior Publication Data

US 2018/0045652 A1 Feb. 15, 2018

(30) Foreign Application Priority Data

Aug. 10, 2016 (JP) .................................. 2016-157751

(51) Int. Cl.
*G01N 21/88* (2006.01)

(52) U.S. Cl.
CPC ............................... *G01N 21/8806* (2013.01)

(58) Field of Classification Search
CPC . G01N 21/8806; G01N 21/8803; G01N 21/00
USPC ............................................ 356/237.2, 237.5
See application file for complete search history.

(56) References Cited

U.S. PATENT DOCUMENTS

| | | |
|---|---|---|
| 2,560,200 A | 7/1951 | Werzyn |
| 3,187,170 A | 6/1965 | Kille |
| 3,893,145 A | 7/1975 | King |
| 3,970,835 A | 7/1976 | Crete |
| 4,051,493 A | 9/1977 | Nakagawa et al. |
| 4,078,170 A | 3/1978 | Sloop |
| 4,081,814 A | 3/1978 | Bulland |
| 4,091,402 A | 5/1978 | Siegel |
| 4,241,988 A | 12/1980 | Lepp |
| 4,259,000 A | 3/1981 | Heredia |
| 4,512,644 A | 4/1985 | Yoshida |
| 4,710,005 A | 12/1987 | Bennett |

(Continued)

FOREIGN PATENT DOCUMENTS

| | | |
|---|---|---|
| JP | H08-114553 A | 5/1996 |
| JP | 2002-116153 A | 4/2002 |

OTHER PUBLICATIONS

U.S. Appl. No. 15/499,123, filed Apr. 27, 2017 in the name of Jiro Umehara.

(Continued)

*Primary Examiner* — Roy M Punnoose
(74) *Attorney, Agent, or Firm* — Oliff PLC

(57) ABSTRACT

An appearance inspection apparatus radiates, with an illumination device, light from a light source as diffused light to an inspection surface included in the inner peripheral surface of an inner ring of a rolling bearing that is an object to be inspected, and photographs the inspection surface with a camera. The illumination device is arranged so that at least a part of the illumination device is present in a space surrounded by the inner peripheral surface of the rolling bearing. The camera is arranged at a position where an angle formed between a straight line connecting a position closest to the camera on the inspection surface to the camera and a line perpendicular to the inspection surface at that position is larger than an incident angle of the diffused light at the position closest to the camera.

6 Claims, 5 Drawing Sheets

(56) References Cited

U.S. PATENT DOCUMENTS

| | | | |
|---|---|---|---|
| 4,731,649 A * | 3/1988 | Chang | G01N 21/9054 |
| | | | 250/223 B |
| 4,752,794 A | 6/1988 | Bohannon | |
| 5,194,885 A | 3/1993 | Spencer | |
| 5,275,364 A | 1/1994 | Burger et al. | |
| 5,592,286 A * | 1/1997 | Fedor | G01N 21/9054 |
| | | | 250/223 B |
| 5,761,550 A | 6/1998 | Kancigor | |
| 6,042,277 A | 3/2000 | Errington | |
| 6,384,863 B1 | 5/2002 | Bronson | |
| 7,957,636 B2 | 6/2011 | Saitoh et al. | |
| 8,736,710 B2 | 5/2014 | Spielberg | |
| 2001/0012393 A1 | 8/2001 | Yonezawa | |
| 2004/0184031 A1 | 9/2004 | Vook et al. | |

OTHER PUBLICATIONS

U.S. Appl. No. 15/666,218, filed Aug. 1, 2017 in the name of Jiro Umehara.
Mar. 28, 2018 Office Action issued in U.S. Appl. No. 15/499,123.

* cited by examiner

APPEARANCE INSPECTION APPARATUS AND APPEARANCE INSPECTION METHOD

INCORPORATION BY REFERENCE

The disclosure of Japanese Patent Application No. 2016-157751 filed on Aug. 10, 2016 including the specification, drawings and abstract, is incorporated herein by reference in its entirety.

BACKGROUND OF THE INVENTION

1. Field of the Invention

The present invention relates to an appearance inspection apparatus and an appearance inspection method, and more particularly, to an apparatus and method for inspecting the appearance of an inner peripheral surface.

2. Description of the Related Art

When inspection is performed on the appearance of the inner peripheral surface of a tubular industrial product such as a rolling bearing but a camera or a light source cannot be inserted into a tubular portion due to its small diameter, a method of photographing the inner peripheral surface from the outside of the tubular portion may be used by using, for example, a fisheye lens 20A as illustrated in FIG. 6. In the appearance inspection method illustrated in FIG. 6, an inner peripheral surface K is illuminated from one end (for example, the lower end) of a rolling bearing that is an object to be inspected, and is photographed from the other end (for example, the upper end) with a camera using the fisheye lens. The inspection of the inner peripheral surface using the fisheye lens as illustrated in FIG. 6 is mentioned as a related art in, for example, Japanese Patent Application Publication No. 8-114553 (JP 8-114553 A).

As described in JP 8-114553 A, however, it is known that the image captured through the fisheye lens is significantly distorted optically. The problem with the appearance inspection based on that image is that the results of inspection cannot be obtained with high accuracy.

SUMMARY OF THE INVENTION

It is one object of the present invention to provide an appearance inspection apparatus and an appearance inspection method in which the accuracy of appearance inspection can be improved when an inspection surface is the inner peripheral surface of a tubular object to be inspected.

An appearance inspection apparatus according to one aspect of the present invention has the following features in its structure. That is, the appearance inspection apparatus includes a photographing device configured to photograph a first inspection surface included in an inner peripheral surface of a tubular object to be inspected, and an illumination device arranged so that at least a part of the illumination device is present in a space surrounded by the inner peripheral surface, and configured to radiate light from a light source to the first inspection surface as diffused light. The photographing device is arranged at a position where an angle formed between a straight line connecting a position closest to the photographing device on the first inspection surface to the photographing device and a line perpendicular to the first inspection surface at the position closest to the photographing device is larger than an incident angle of the diffused light at the position closest to the photographing device. By arranging the photographing device at the position where the angle formed between the straight line connecting the position closest to the photographing device on the first inspection surface to the photographing device and the line perpendicular to the first inspection surface at the position closest to the photographing device is larger than the incident angle of the diffused light at the position closest to the photographing device, light that is specularly reflected by the first inspection surface is prevented from entering the photographing device. Therefore, the ratio of light that is diffusely reflected from the first inspection surface to enter the photographing device can be increased. As a result, the ratio of a difference in the intensity of the light that is diffusely reflected to enter the photographing device depending on regions due to a difference in surface roughness such as a shoe mark can be increased relative to the total intensity of the light that enters the photographing device. Thus, the contrast of the color density based on the difference in the surface roughness is increased in an image captured by the photographing device. Accordingly, the difference in the surface roughness such as a shoe mark that is present on the first inspection surface can be detected with high accuracy based on the color density of the captured image.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

Figure 1:
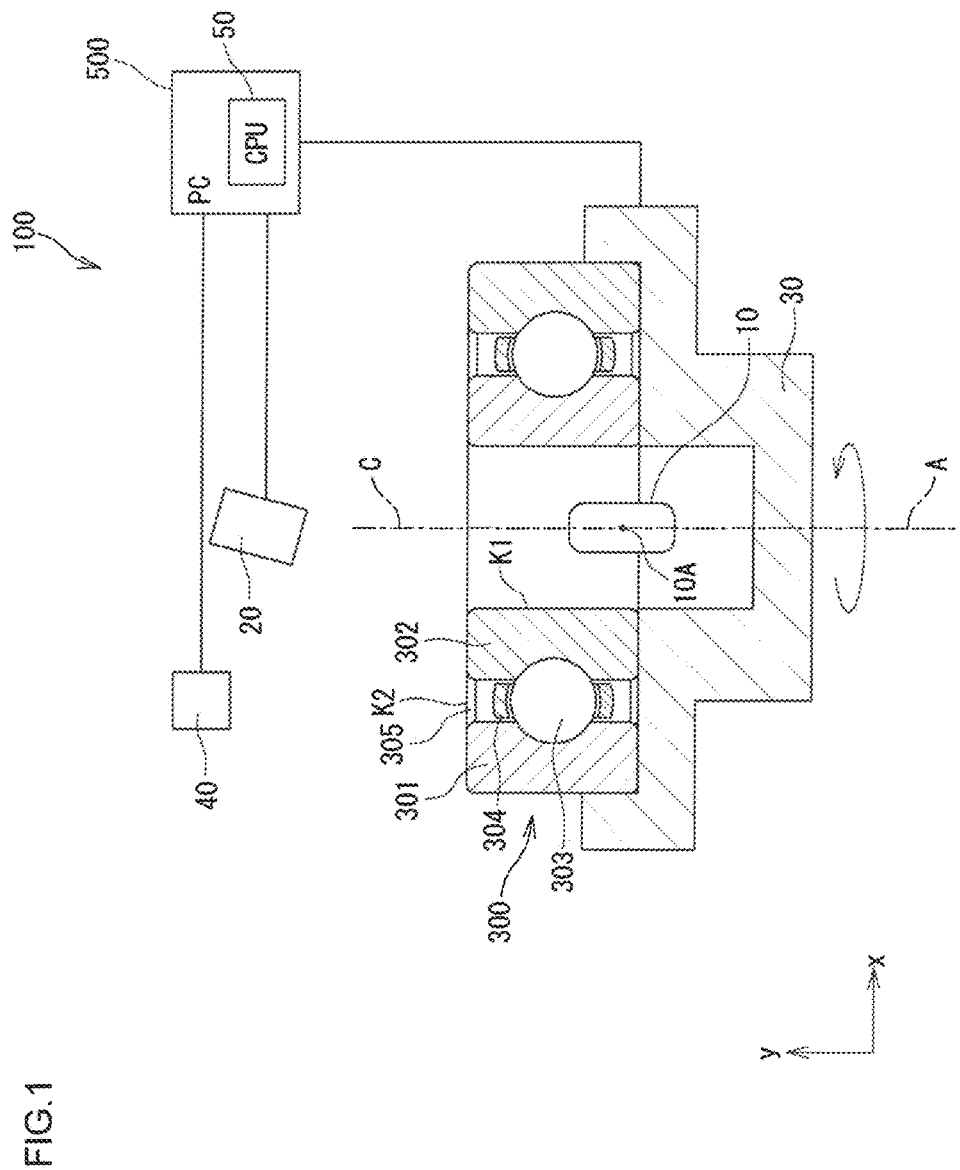
FIG. 1 is a schematic front view of an appearance inspection apparatus according to an embodiment.

Preferred embodiments are described below with reference to the drawings. In the following description, the same parts and constituent elements are denoted by the same reference symbols. The names and functions of those parts and constituent elements are also the same. Thus, description of those parts and constituent elements is not repeated.

A first embodiment is described below. An appearance inspection apparatus 100 according to this embodiment inspects the appearance of an industrial product having a high reflectance on its surface, that is, having gloss on its surface. In particular, the appearance inspection apparatus 100 inspects the inner peripheral surface of a cylindrical industrial product. An object to be inspected by the appearance inspection apparatus 100 is, for example, a rolling bearing. In the following description, the appearance inspection apparatus 100 inspects an inspection surface included in the inner periphery of an inner ring of the rolling bearing. A rolling bearing 300 to be subjected to appearance inspection performed by the appearance inspection apparatus 100 includes an outer ring 301, an inner ring 302, a plurality of rolling elements 303, a cage 304, and bearing seals 305.

FIG. 1 is a schematic front view of the appearance inspection apparatus 100 according to this embodiment. Referring to FIG. 1, the appearance inspection apparatus 100 includes a light source 10A such as a light emitting diode (LED). The appearance inspection apparatus 100 includes an illumination device 10 and a camera 20. The illumination device 10 radiates light from the light source 10A to a first inspection surface K1 included in the inner periphery of the inner ring 302 of the rolling bearing 300 that is the object to be inspected. The camera 20 is an example of a photographing device configured to capture an image of the first inspection surface K1. The photographing device may be an image sensor or the like.

It is preferred that the appearance inspection apparatus 100 further includes a sensor 40 serving as a displacement sensor. The appearance inspection apparatus 100 including the sensor 40 is described later in a fourth embodiment. The appearance inspection apparatus 100 according to each of the first embodiment to a third embodiment does not include the sensor 40.

The rolling bearing 300 is arranged on a rotary table 30 having a horizontal loading surface so that a central axis C corresponding to a rotation axis of the rolling bearing 300 is identical to a rotation center A of the rotary table 30. The rotation center A is set in a vertical direction, and a direction of the central axis C of the rolling bearing 300 arranged on the rotary table 30 is the vertical direction.

In the following description, the horizontal direction is defined as an x direction, and the right side in FIG. 1 is defined as a positive side of the x direction (referred to also as a +x side). The left side in FIG. 1 is defined as a negative side of the x direction (referred to also as a −x side). The vertical direction is defined as a y direction, and the upper side in FIG. 1 is defined as a positive side of the y direction (referred to also as a +y side). The lower side in FIG. 1 is defined as a negative side of the y direction (referred to also as a −y side).

The camera 20 is arranged above (on the +y side of) the end face of the rolling bearing 300 on the +y side at a position spaced away from the end face. The camera 20 is arranged so as to be oriented toward the inner peripheral surface of the inner ring 302. The camera 20 is connected to a computer (personal computer (PC)) 500 serving as a controller, and inputs the captured image to the PC 500. The PC 500 includes a central processing unit (CPU) 50 for controlling the PC 500.

The illumination device 10 is arranged so that at least a part of the illumination device 10 is present in a space surrounded by the inner peripheral surface of the rolling bearing 300 arranged on the rotary table 30. The illumination device 10 radiates the light from the light source 10A to the first inspection surface K1 as diffused light. For example, the light source 10A and the illumination device 10 are arranged on a straight line including the central axis C below a position corresponding to a half of the length (height) of the rolling bearing 300 in the y direction (at a position spaced away from the half position in the −y direction). The tip portion (uppermost portion) of the illumination device 10 is arranged above (on the +y side of) the lowermost point (bottom surface) of the rolling bearing 300 in the y direction. The light source 10A is not limited to the LED, and may be the end of a transmission path such as an optical fiber configured to transmit light radiated from a light source such as an LED arranged at a remote place. The illumination device 10 radiates the light from the light source 10A to the entire first inspection surface K1 as diffused light having a low directivity by using a diffuser, a reflector, or the like (not illustrated). The light radiated by the illumination device 10 is preferably white light. With the white light, the difference of portions with defect and portions without defect is clearer than red, green, or blue light. Therefore, the detection accuracy for a defect can further be improved. In the following description, the illumination device 10 refers to a light emitting surface, that is, a radiation surface itself.

The rotary table 30 is rotatable as indicated by an arrow in FIG. 1 in accordance with control performed by the PC 500. Through the rotation of the rotary table 30, the rolling bearing 300 arranged on the rotary table 30 rotates about the central axis C as a rotation center to change the surface that faces the camera 20.

The principle of inspection is described below. The appearance inspection apparatus 100 radiates diffused light to the first inspection surface K1 with the illumination device 10. The appearance inspection apparatus 100 inspects the first inspection surface K1 for a defect based on the intensity of light that is reflected by the first inspection surface K1 to enter the camera 20. The defect on the first inspection surface K1 that is inspected by the appearance inspection apparatus 100 is, for example, a defect called a shoe mark. The shoe mark refers to small irregularities due to a difference in surface roughness or the like, which is caused by contact between a surface and foreign matter such as grinding swarf mostly in a surface grinding step of the manufacturing process. Industrial products having gloss obtained by grinding or coating their surfaces have a high reflectance on their surfaces. The surface of the rolling bearing 300 is also ground, and therefore has a high reflectance. When the first inspection surface K1 has a range with the above-mentioned defect and a range without the above-mentioned defect, there is a difference between the amounts of reflection from the respective ranges. By using the difference between the amounts of reflection, the appearance inspection apparatus 100 inspects the first inspection surface K1 for a defect based on the amounts of reflection from the first inspection surface K1.

Figure 2:
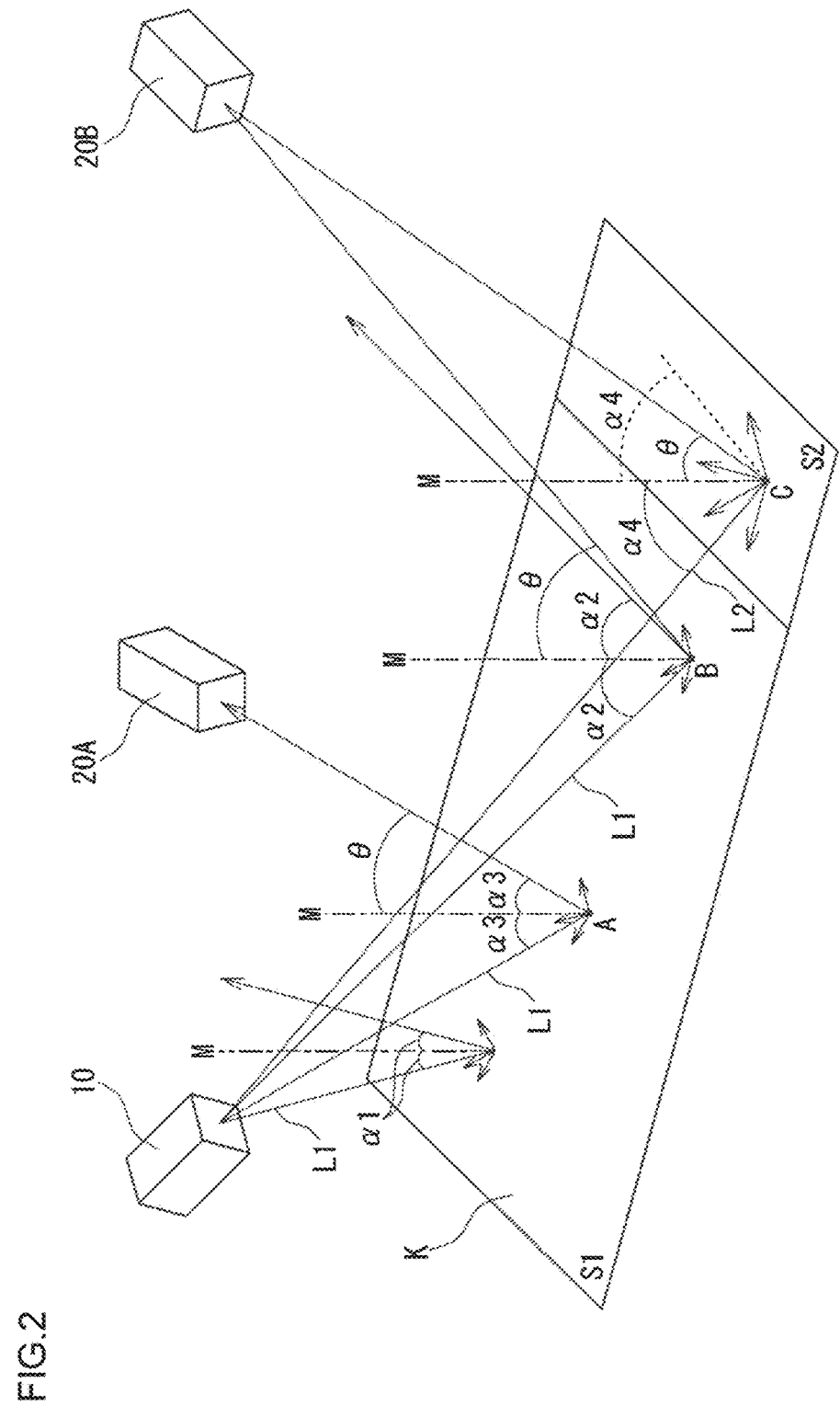
FIG. 2 is a schematic view for describing the principle of inspection to be performed by the appearance inspection apparatus.

Referring to FIG. 2, the principle of inspection to be performed by the appearance inspection apparatus 100 is described. FIG. 2 is a view of an inspection surface K that is viewed obliquely from the top. The illumination device 10 and cameras 20A and 20B are arranged above the inspection surface K. The inspection surface K has a range S1 with a shoe mark and a range S2 without a shoe mark. In the range S1, the surface is ground in a state in which foreign matter such as grinding swarf is pressed against the surface. Therefore, the surface roughness of the range S1 is smaller than the surface roughness of the range S2. Thus, the intensity of light L1 that is radiated to the range S1 and is specularly reflected by the inspection surface K is higher than the intensity of light L2 that is radiated to the range S2 and is specularly reflected by the inspection surface K. In contrast, the intensity of the light L2 that is radiated to the range S2 and is diffusely reflected by the inspection surface K is higher than the intensity of the light L1 that is radiated to the range S1 and is diffusely reflected by the inspection surface K.

An angle θ is defined as an angle formed between a straight line connecting an arbitrary position on the inspection surface K to a central point (point on a photographing axis) of a lens (not illustrated) of the camera and a line M perpendicular to the inspection surface K at that position.

When the camera is arranged in a direction in which an incident angle α of diffused light and the angle θ are equal to each other at a certain position on the inspection surface K (θ=α), light that is specularly reflected at that position enters the camera. Further, light that is diffusely reflected at other positions enters the camera.

In FIG. 2, the camera 20A is arranged at a position where light that is specularly reflected from any one of the positions on the inspection surface K (for example, a point A in FIG. 2) enters the camera 20A (θ=α). That is, the camera 20A and the light source of the illumination device 10 have a positional relationship that satisfies θ=α at any one of the positions on the inspection surface K (second positional relationship). Light that is specularly reflected in the range S1, light that is diffusely reflected in the range S1, and light that is diffusely reflected in the range S2 enter the camera 20A. When the inspection surface K is a glossy surface, the ratio of the intensity of the light that is specularly reflected to enter the camera 20A is significantly higher than the ratio of the intensity of the light that is diffusely reflected to enter the camera 20A. Therefore, the difference in the intensity between the light that is diffusely reflected in the range S1 and the light that is diffusely reflected in the range S2 is significantly small relative to the total intensity of the reflected light that enters the camera 20A. Thus, it may be difficult to detect the difference in the surface roughness between the ranges S1 and S2, that is, the inspection surface K based on the difference in the light intensity.

In FIG. 2, the camera 20B is arranged in a direction in which light that is specularly reflected from any positions on the inspection surface K (for example, points B and C in FIG. 2) does not enter the camera 20B (θ≠α). That is, the camera 20B and the light source of the illumination device 10 have a positional relationship that satisfies θ≠α at any positions on the inspection surface K (first positional relationship). Neither the light that is specularly reflected in the range S1 nor the light that is specularly reflected in the range S2 enters the camera 20B. Instead, the light that is diffusely reflected in the range S1 and the light that is diffusely reflected in the range S2 enter the camera 20B. Therefore, the difference in the intensity between the light that is diffusely reflected in the range S1 and the light that is diffusely reflected in the range S2 is large relative to the total intensity of the reflected light that enters the camera 20B. Thus, it is easy to detect the difference in the surface roughness between the ranges S1 and S2, that is, the inspection surface K based on the difference in the light intensity.

Figure 3:
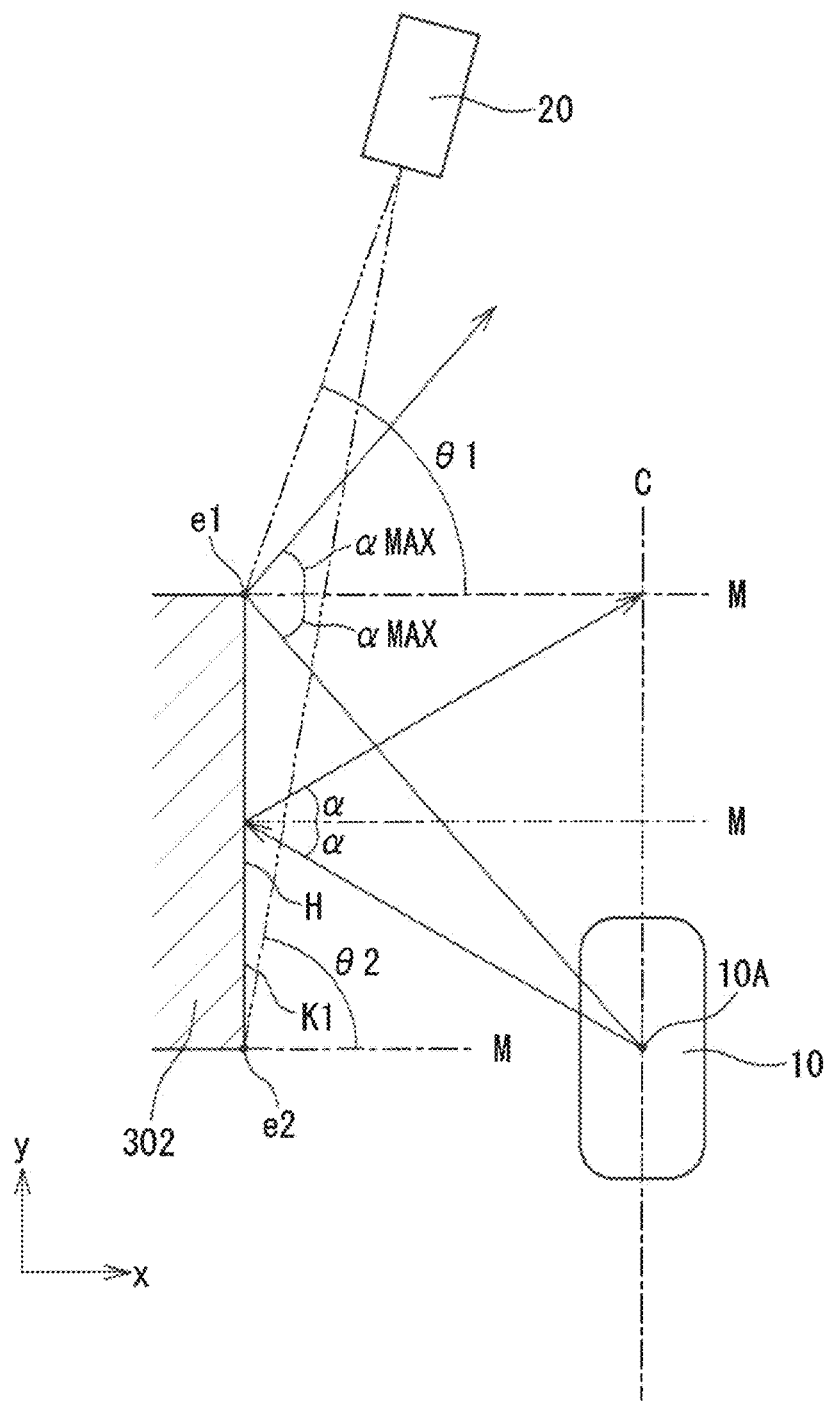
FIG. 3 is a schematic plan view illustrating a main part of the appearance inspection apparatus.

A positional relationship between the camera 20 and the illumination device 10 of the appearance inspection apparatus 100 is described with reference to FIG. 3. FIG. 3 is a schematic plan view illustrating a main part of the appearance inspection apparatus 100. FIG. 3 illustrates a part of a cross section of the inner ring 302, which is taken along a plane (reference plane) including the central axis C and the camera 20. In FIG. 3, the light source 10A is located at the same height as that of a point e2 in the y direction.

The incident angle α of the diffused light at each point on the first inspection surface K1 decreases as the distance from the light source 10A decreases, and increases as the distance from the light source 10A increases. A straight line H is defined as the inner periphery of the inner ring 302 in its cross section taken along the reference plane, that is, a straight line extending from a point e1 to the point e2 in FIG. 3. The point e1 is a point on the end face of the rolling bearing 300 on the +y side, and the point e2 is a point on the end face of the rolling bearing 300 on the −y side. When the first inspection surface K1 includes the straight line H and the illumination device 10 is arranged below a position corresponding to a half of the length (height) of the rolling bearing 300 in the y direction (at a position spaced away from the half position in the −y direction), the point e1 on the straight line H is farthest from the light source 10A. Therefore, the incident angle α is largest (incident angle αMAX) at the point e1 among all the points on the straight line H. Thus, the incident angle α satisfies 0≤α≤αMAX at all the points on the straight line H. In order that the camera 20 and the light source 10A may have a positional relationship in which the angle θ and the incident angle α satisfy θ≠α at all the positions on the first inspection surface K1, it is only necessary to arrange the camera 20 in a direction in which θ>αMAX is satisfied on the reference plane.

The angle θ at each point on the first inspection surface K1 decreases as the distance from the camera 20 (that is, the central point of the lens (not illustrated) of the camera 20) decreases, and increases as the distance from the camera 20 increases. Referring to FIG. 3, the smallest angle is an angle θ1 at the point e1 closest to the camera 20 among all the points on the straight line H. The largest angle is an angle θ2 at the point e2 farthest from the camera 20 among all the points on the straight line H. That is, the angle θ satisfies θ1≤θ≤θ2 at all the points on the straight line H.

Thus, the angle θ satisfies θ>αMAX by setting θ1>αMAX.

The camera 20 illustrated in FIG. 3 is located in a direction in which θ1>αMAX is satisfied. The camera 20 is arranged at the position illustrated in FIG. 3. Thus, light that is specularly reflected at any positions on the first inspection surface K1 does not enter the camera 20. That is, the light that is specularly reflected by the first inspection surface K1 does not enter the camera 20, but the light that is diffusely reflected by the first inspection surface K1 enters the camera 20. Thus, the camera 20 is arranged at a position on the reference plane where θ1>αMAX is satisfied. Accordingly, the difference in the surface roughness of the first inspection surface K1 can be detected based on the intensity of the light that is diffusely reflected by the first inspection surface K1 to enter the camera 20.

Figure 4:
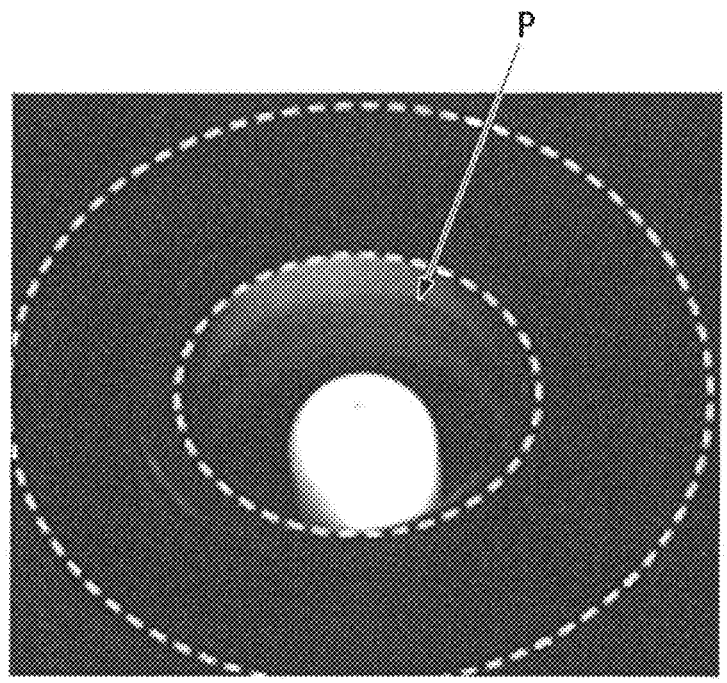
FIG. 4 is an image captured by photographing a first inspection surface by the appearance inspection apparatus according to the embodiment.

FIG. 4 is an image captured by photographing the first inspection surface K1 with the camera 20 of the appearance inspection apparatus 100. FIG. 4 is a captured image in a case where a part of the inner periphery of the inner ring 302 is the first inspection surface K1. Referring to FIG. 4, the image captured by the appearance inspection apparatus 100 clearly shows a black line P on the inner periphery of the inner ring 302. The line P indicates a shoe mark that is present on the inner periphery of the inner ring 302. In the appearance inspection apparatus 100, the first inspection surface K1 is photographed while the camera 20 is arranged at the position illustrated in FIG. 3. Thus, the contrast of the color density of the captured image is increased. Therefore, the captured image clearly shows a difference in the color density between a range with a large surface roughness of the first inspection surface K1 due to a shoe mark or the like and a range with a small surface roughness of the first inspection surface K1.

For example, the CPU 50 of the PC 500 executes analysis processing to analyze the color density, that is, the lightness of the captured image (FIG. 4) from the camera 20. In this manner, the presence of a shoe mark on the first inspection surface K1 can be detected. The presence of a shoe mark may be detected through a user's visual check to be conducted by displaying the captured image on a display (not illustrated) of the PC 500.

Figure 5:
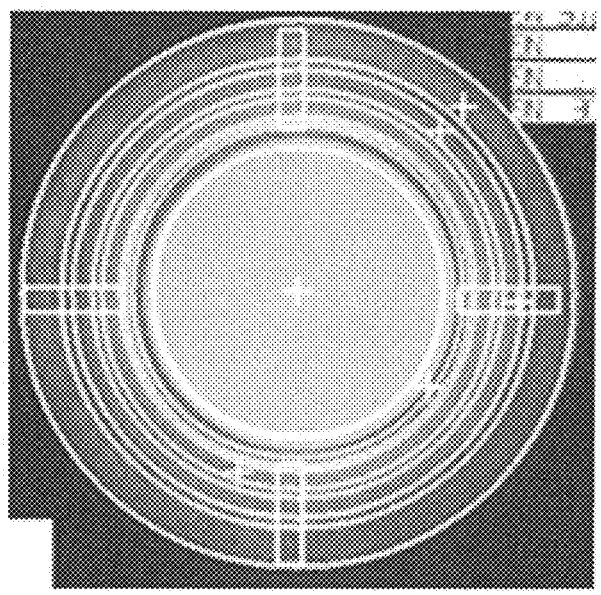
FIG. 5 is an image captured by photographing the first inspection surface by a related-art appearance inspection apparatus.
Figure 6:
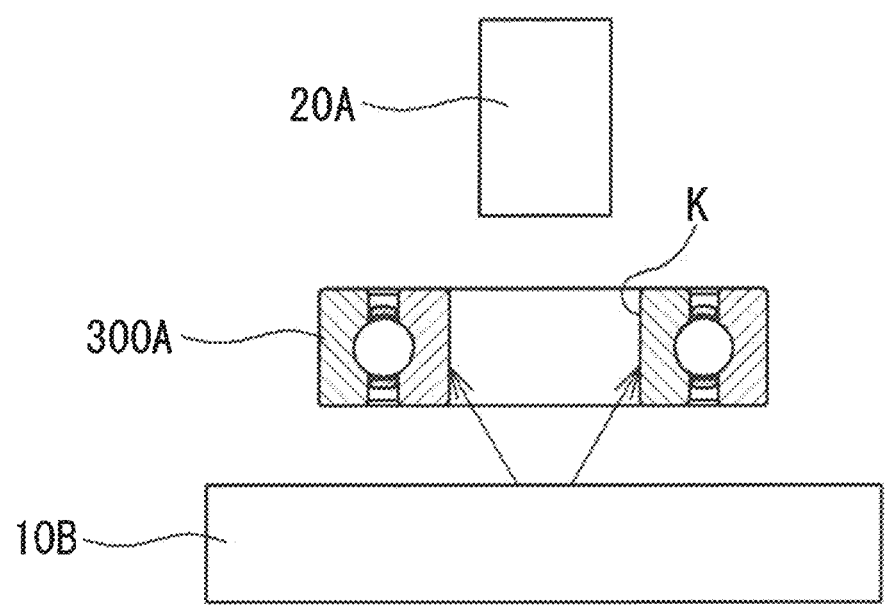
FIG. 6 is a schematic view illustrating the related-art appearance inspection apparatus.

Effects of the first embodiment are described below. Effects of the appearance inspection performed by the appearance inspection apparatus 100 according to this embodiment are verified through comparison to a result of inspection performed by a related-art appearance inspection apparatus. FIG. 5 is an image captured by the related-art appearance inspection apparatus as a result of inspection. FIG. 6 is a schematic view of the structure of the related-art appearance inspection apparatus used in the comparison. The image in FIG. 5 captures the same rolling bearing as that in the captured image in FIG. 4 as the subject of photographing and the entire inner peripheral surface of the inner ring is the inspection surface K.

Referring to FIG. 6, in the related-art appearance inspection apparatus, an illumination device 10B is arranged so as to face the end face of a rolling bearing 300A on the −y side, and directly radiates light to the rolling bearing 300A. A camera 20A is provided with a fisheye lens (not illustrated), and is arranged so as to face the end face of the rolling bearing 300A on the +y side.

Referring to FIG. 5, the image is captured by the related-art appearance inspection apparatus through the fisheye lens. Therefore, the image is distorted optically. In particular, the captured image of the inspection surface K is more distorted at a position closer to the edge of the image, that is, closer to the end face of the rolling bearing 300A on the +y side. Therefore, the contrast of the color density is low as a whole, and the deep color region corresponding to the line P in FIG. 4 is not observed through a visual check.

As described above, in the appearance inspection apparatus 100, the optical distortion of the captured image is suppressed by photographing the inspection surface with the camera 20 without using the fisheye lens. Thus, the contrast of the color density can be increased. In the appearance inspection apparatus 100, the camera 20 and the illumination device 10 have the positional relationship of FIG. 3, and therefore the appearance inspection can be performed by using the difference in the intensity of diffusely reflected light that enters the camera 20. Thus, the difference in the surface roughness of the first inspection surface K1 is clearly shown as the difference in the color density of the captured image. Accordingly, the defect on the first inspection surface K1 that is the difference in the surface roughness such as a shoe mark can be detected with high accuracy.

A second embodiment is described below. The captured image in FIG. 4 is an example of the case where the first inspection surface K1 is a part of the inner peripheral surface of the inner ring 302. The first inspection surface K1 may cover a range wider than that of the captured image in FIG. 4. For example, the first inspection surface K1 may be the entire inner peripheral surface of the inner ring 302. In this case, in the appearance inspection apparatus 100, the rotary table 30 rotates in accordance with the control performed by the PC 500, and the PC 500 causes the camera 20 to photograph the first inspection surface K1 at predetermined timings along with the rotation. Thus, the first inspection surface K1 that is, for example, the entire inner peripheral surface of the inner ring 302 is photographed a plurality of times.

In the first and second embodiments described above, the light source 10A and the illumination device 10 are arranged on the straight line including the rotation axis C. By arranging the light source 10A and the illumination device 10 at this position, the positional relationship between the first inspection surface K1 and the illumination device 10 is fixed even when the rolling bearing 300 is rotated by the rotary table 30 as in the appearance inspection apparatus 100 according to the second embodiment. Therefore, the color density of the captured image is stable.

A third embodiment is described below. The position of the illumination device 10 is not limited to the position on the straight line including the rotation axis C, and may be any position as long as the first inspection surface K1 can be irradiated with light. It is preferred that the illumination device 10 be arranged at a position that does not obstruct straight lines connecting every point on the first inspection surface K1 to the camera 20. Specifically, referring to FIG. 3, the illumination device 10 is arranged below a straight line connecting the camera 20 to the point e2 (at a position spaced away from the straight line in the −y direction). As illustrated in FIG. 3, the tip (end on the +y side) of the illumination device 10 is formed into a rounded surface, and therefore the illumination device 10 can be prevented from obstructing the straight line connecting the point e2 to the camera 20 more securely. Thus, the illumination device 10 is not located in the photographing range of the camera 20.

A fourth embodiment is described below. The appearance inspection apparatus 100 according to the fourth embodiment further includes the sensor 40 as illustrated in FIG. 1. The sensor 40 is a displacement sensor. The sensor 40 measures, in a noncontact manner by using a laser beam or the like, a distance to a second inspection surface K2 included in the surface of the rolling bearing 300 arranged on the rotary table 30. For example, the sensor 40 measures, in a noncontact manner by using a laser beam or the like, a distance to a sealing device provided on the end face of the rolling bearing 300 on the +y side, which is arranged on the rotary table 30. The sealing device is, for example, the bearing seal 305 provided on the end face of the rolling bearing 300 as illustrated in FIG. 1. As another example, the sealing device may be a shield plate. The sensor 40 measures the distance to the second inspection surface K2 while the second inspection surface K2 is defined as a surface included in the end face of the rolling bearing 300 where the bearing seal 305 is arranged. The sensor 40 is located above the bearing seal 305 of the rolling bearing 300 arranged on the rotary table 30 (at a position spaced away from the bearing seal 305 in the +y direction). In addition, the sensor 40 is provided at a position that does not obstruct the straight lines connecting every position on the first inspection surface K1 to the camera 20. By providing the sensor 40 at this position, the sensor 40 is not located in the photographing range when the camera 20 photographs the first inspection surface K1. Thus, the appearance inspection for the first inspection surface K1 and the appearance inspection for the second inspection surface K2 can be performed simultaneously.

When the rolling bearing 300 rotates about the rotation axis C through the rotation of the rotary table 30 and the camera 20 photographs the first inspection surface K1 along with the rotation as in the appearance inspection apparatus 100 according to the second embodiment, the distance to the second inspection surface K2 can be measured simultaneously by providing the sensor 40 as described above. That is, in the appearance inspection apparatus 100 according to the fourth embodiment, the camera 20 photographs the first inspection surface K1 included in the inner peripheral surface of the inner ring 302, and the sensor 40 measures the distance to the second inspection surface K2 included in the surface where the bearing seal 305 is arranged. That is, in the appearance inspection apparatus 100 according to the fourth embodiment, the captured image of the first inspection surface K1 and the distance to the second inspection surface K2 are obtained through one detecting operation.

When a measured value is input from the sensor 40, the PC 500 executes analysis such as comparison between the distance to the second inspection surface K2 and an appropriate distance stored in advance. Thus, fitting failure of the sealing device such as the bearing seal 305 is detected in the appearance inspection. Accordingly, the sealing device can be inspected for fitting failure along with the appearance inspection for the first inspection surface K1.

Thus, in the appearance inspection apparatus 100 according to the fourth embodiment, the inspection time can be reduced as compared to a case where the above-mentioned two types of inspection are performed through different inspecting operations. The appearance inspection apparatus can be downsized as compared to a case where appearance inspection apparatuses are prepared separately for the two types of inspection.

It should be understood that the embodiments disclosed herein are illustrative but are not limitative in all respects. The scope of the present invention is defined by the claims rather than the description above, and is intended to encompass meanings of equivalents to the elements in the claims and all modifications within the scope of the claims.

According to the present invention, the accuracy of appearance inspection can be improved.

What is claimed is:

1. An appearance inspection apparatus, comprising:
a photographing device configured to photograph a first inspection surface included in an inner peripheral surface of a tubular object to be inspected; and
an illumination device arranged so that at least a part of the illumination device is present in a space surrounded by the inner peripheral surface, and configured to radiate light from a light source to the first inspection surface as diffused light, wherein
the photographing device is arranged at a position where an angle formed between a straight line connecting a position closest to the photographing device on the first inspection surface to the photographing device and a line perpendicular to the first inspection surface at the position closest to the photographing device is larger than an incident angle of the diffused light at the position closest to the photographing device.

2. The appearance inspection apparatus according to claim 1, wherein the illumination device is arranged at a position that does not obstruct straight lines connecting every position on the first inspection surface to the photographing device.

3. The appearance inspection apparatus according to claim 1, further comprising a movement device configured to rotate at least one of the photographing device and the object to be inspected about a central axis, so that a positional relationship between the photographing device and the object to be inspected is changed relatively, wherein
the photographing device is configured to photograph the entire inner peripheral surface by photographing the inner peripheral surface a plurality of times while the positional relationship is changed by the movement device.

4. The appearance inspection apparatus according to claim 1, wherein
the object to be inspected is a rolling bearing including an inner ring and an outer ring, and
the first inspection surface is included in an inner peripheral surface of the inner ring.

5. The appearance inspection apparatus according to claim 1, further comprising a displacement sensor capable of measuring a distance to a second inspection surface of the object to be inspected, which is different from the first inspection surface, wherein
the displacement sensor is arranged at a position that does not obstruct the straight lines connecting every position on the first inspection surface to the photographing device.

6. An appearance inspection method for a tubular object to be inspected using an image captured by photographing, with a photographing device, an inspection surface included in an inner peripheral surface of the object to be inspected, the appearance inspection method comprising:
radiating diffused light to the inspection surface with an illumination device including a light source; and
photographing the inspection surface, which is irradiated with the diffused light, with the photographing device from a position where an angle formed between a straight line connecting a position closest to the photographing device on the inspection surface to the photographing device and a line perpendicular to the inspection surface at the position closest to the photographing device is larger than an incident angle of the diffused light at the position closest to the photographing device.

* * * * *